(12) United States Patent
Hirokawa et al.

(10) Patent No.: US 7,602,880 B2
(45) Date of Patent: Oct. 13, 2009

(54) X-RAY CT APPARATUS

(75) Inventors: Koichi Hirokawa, Tokyo (JP); Taiga Goto, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 37 days.

(21) Appl. No.: 12/066,469

(22) PCT Filed: Sep. 15, 2006

(86) PCT No.: PCT/JP2006/318344

§ 371 (c)(1),
(2), (4) Date: Mar. 11, 2008

(87) PCT Pub. No.: WO2007/032462

PCT Pub. Date: Mar. 22, 2007

(65) Prior Publication Data

US 2009/0046833 A1 Feb. 19, 2009

(30) Foreign Application Priority Data

Sep. 15, 2005 (JP) .............................. 2005-268748

(51) Int. Cl.
*H05G 1/44* (2006.01)
(52) U.S. Cl. .......................................... 378/8; 378/108
(58) Field of Classification Search ...................... 378/4, 378/7, 8, 16, 19–20, 97, 108
See application file for complete search history.

(56) References Cited

U.S. PATENT DOCUMENTS

| | | | |
|---|---|---|---|
| 5,400,378 A * | 3/1995 | Toth | 378/16 |
| 7,072,437 B2 * | 7/2006 | Seto | 378/20 |
| 2004/0202277 A1 | 10/2004 | Okumura et al. | |
| 2007/0076842 A1 * | 4/2007 | Tkaczyk et al. | 378/5 |

FOREIGN PATENT DOCUMENTS

| | | |
|---|---|---|
| JP | 7-124152 | 5/1995 |
| JP | 2004-305527 | 11/2004 |

\* cited by examiner

*Primary Examiner*—Hoon Song
(74) *Attorney, Agent, or Firm*—Cooper & Dunham, LLP

(57) ABSTRACT

[Problems] To provide an X-ray CT apparatus capable of easily comparing image quality supposed to be obtained when not using a X-ray dose optimization function and image quality supposed to be obtained when using the X-ray dose optimization function at the stage of scan planning.

[Means for Solving Problems] A 3-dimensional model of an object to be examined (17) is generated from scanogram projection data (S170). An image noise dispersion value corresponding to an imaging region of the object is predicted from the 3-dimensional model.

The predicted image noise dispersion value is compared to a desired value of the image index value inputted by a user so as to calculate a modulation pattern of the irradiation X-ray amount (S200).

By predicting the image quality supposed to be obtained when using and not using the X-ray dose optimization function, each of the predicted results is displayed so as to be compared on a display device (5) (S230).

8 Claims, 11 Drawing Sheets

FIG. 11

| NOT USING SCAN DOSE OPTIMIZATION FUNCTION | USING SCAN DOSE OPTIMIZATION FUNCTION |
|---|---|
| TUBE CURRENT [mA]<br>250<br><br>CTDI [mGy]<br>15.4<br><br>IMAGE SD ESTIMATED VALUE<br>8.51 | TUBE CURRENT [mA]<br>200<br><br>CTDI [mGy]<br>12.3<br><br>IMAGE SD ESTIMATED VALUE<br>9.52 |

34

X-RAY CT APPARATUS

TECHNICAL FIELD

The present invention relates to an X-ray CT apparatus, more particularly to a single slice or multi slice X-ray CT apparatus for irradiating X-ray of fan beam (sector form beam) or cone beam (conical shape or pyramid shape beam) to an object to be examined, measuring the X-ray transmitted through the object by an X-ray detector and acquiring a tomographic image of the object by back projecting the measurement data from multiple directions, which is capable of obtaining CT images with desired image quality.

BACKGROUND ART

A multi slice X-ray CT apparatus is generally configured, as shown in FIG. 3, to obtain projection data of an object 17 by irradiating X-ray beams of cone beam that are pyramid shape from an X-ray tube 8 and measuring X-ray after transmitting through the object by a detector 11 in which detection elements 18 are arranged two-dimensionally (in channel direction and row direction).

Also in single slice X-ray CT apparatus, projection data of the object 17 is obtained by irradiating X-ray beams of fan beam that is sector form beam from the X-ray tube 8 to the object 17 using the detector 11 in which detector elements are arranged in one row that is one-dimensionally (in channel direction), and measuring the X-ray after transmitting through the object 17.

In either case, projection data is obtained from multiple directions by rotating the X-ray tube 8 and the detector 11 which are facing each other around the object 17, and performing reconstruction filtering process for deblurring, then a tomgraphic image of the object 17 is reconstructed by back projection.

Projection data is obtained at discrete X-ray tube position (hereinafter, it is referred to as "view"), and the obtained projection data is referred to as "projection data in the relevant view". The number of views per one rotation generally extends to several hundreds to several thousands. The operation for obtaining projection data of the view number necessary for reconstructing one tomographic image is referred to as a "scan". Also, projection data for one view is formed by data for the number of channels times the number of rows of the detector 11 (for the single slice X-ray CT apparatus, it is calculated as in the case that the number of row=1) as previously described.

In the past, there have been X-ray CT apparatus, in order to perform scanning which satisfies an image SD (Standard Deviation) value necessary for image reconstruction, capable of performing scanning by calculating an elliptic cross section model of an object from scanogram projection data obtained by scanogram imaging in one direction, and calculating appropriate tube current value from the projected area of the elliptic cross section, aspect ratio of the elliptic cross section and the desired image SD value inputted by an operator. Hereinafter, in setting stage of scan planning, a function for inputting desired image quality index value (image SD value, etc.) within the scanning range and properly modulating an irradiation X-ray dose (scan dose) to satisfy the image quality index value thereof is referred to as a X-ray dose optimization function.

However, without knowledge of the suitable value as the desired image quality index value prior to scanning, actual acquisition of proper images can not be carried out even with the usage of the above-described X-ray dose optimization function.

To solve this problem, an X-ray CT apparatus for generating and displaying simulated images corresponding to the set scanning condition and the desired image noise index value (image SD value) is disclosed in Patent Document 1.

Patent Document 1: JP-A-2004-329661

DISCLOSURE OF THE INVENTION

Problems to be Solved

However, in regard to, for example, the merit of the X-ray dose optimization function improves the image quality uniformity in the body axis direction, since the above-mentioned conventional technique does not have the function for easily comparing the image quality between using and not using the X-ray dose optimization function, it is not capable of easily comparing the quality of the images reconstructed when using and not using the X-ray dose optimization function.

The improvement of image quality uniformity in the body axis direction is carried out by modulation of the irradiated X-ray dose (scan dose) on the arbitrary cross-section of the object so as to satisfy the desired image quality index value, and has a significant advantageous effect in image quality in relation to the X-ray dose optimization function, thus it is crucial to properly suppose the efficacy in the case of using the X-ray dose optimization function prior to the actual scanning.

Also, by using the X-ray dose optimization function, there are regions of the object to be examined wherein the image quality gets more deteriorated than the case of not using the X-ray dose optimization function due to the difference in cross-sections of the object, and such demerit can not be acknowledged in the conventional technique due to the incapability of easily comparing image quality between using and not using the X-ray dose optimization function.

The objective of the present invention is to solve the above-mentioned problems, and to provide an X-ray CT apparatus capable of easily comparing the image quality supposed to be obtained when not using the X-ray dose optimization function upon scan planning and the image quality supposed to be obtained when using the X-ray dose optimization function.

Means to Solve the Problems

In order to achieve the above-mentioned objectives, the X-ray CT apparatus related to the present invention comprises:

an X-ray source having an X-ray tube for irradiating X-rays and an X-ray tube control device for controlling the X-ray tube;

an X-ray detector being arranged facing the X-ray source having an object to be examined therebetween, for detecting the X-rays and outputting X-ray projection data;

rotation means on which the X-ray source and the X-ray detector are mounted, and is capable of rotating:

image processing means for reconstructing a tomographic image based on the X-ray projection data;

input means for inputting image quality index value indicating the desired index of image quality with respect to the tomographic image obtained by the image processing means;

model generation means for generating an object cross-section model in the body-axis direction of the object from scanogram data of the object;

optimization means for setting an irradiation dose modulation curve indicating the desired proper X-ray irradiation dose based on the object cross-section model and the image quality index value, and modulating the X-ray irradiation dose based on the set irradiation dose modulation curve;

image estimation means for estimating the image quality of the supposed image using optimization supposed to be obtained upon rotation imaging while performing modulation of the irradiated X-ray dose based on the irradiation dose modulation curve and the image quality of the supposed image without optimization supposed to be obtained upon rotation imaging without performing modulation of the X-ray irradiation dose based on the irradiation dose modulation curve; and display means for displaying the estimation result of image quality supposed by the image quality estimation means.

EFFECT OF THE INVENTION

In accordance with the present invention, it is possible to easily and concretely compare, prior to the actual scanning, the image quality of the image supposed to be obtained in the case of using the X-ray dose optimization function and the image quality of the image supposed to be obtained in the case of not using the X-ray dose optimization function.

It also is possible, in the case that a target region of the object is specified upon scan planning, to specifically display the difference between the image quality of the portion equivalent to the target region in the image supposed to be obtained in the case of using the X-ray dose optimization function and the image quality of the portion equivalent to the target region in the image supposed to be obtained in the case of not using the X-ray dose optimization function.

BEST MODE FOR CARRYING OUT THE INVENTION

Hereinafter, an embodiment of the present invention will be described in detail referring to the diagrams. It should be noted that the present invention is not intended to be limited to the embodiments described below.

<Hardware Configuration>

Hereinafter, on the basis of FIG. 1~FIG. 4, hardware configuration of the X-ray CT apparatus to which the present invention is applied will be described. FIG. 1 is a general overview of an X-ray CT apparatus 50 to which the present invention is to be applied, FIG. 2 is a general configuration diagram of the X-ray CT apparatus 50, FIG. 3 is a pattern diagram illustrating the configuration of the detector 18 of the X-ray CT apparatus 50 and the relationship between the detector 18 and X-ray irradiation, and FIG. 4 shows the relationship among a scanner 1, a patient table 2 of the X-ray CT apparatus 50 and an object 18 viewed from the lateral direction.

As shown in FIG. 1, the X-ray CT apparatus 50 to which the present invention is applied comprises the scanner 1, the patient table 2, a console 3, a top-panel 4 of the patient table 2, a display device 5 and an operation device 6.

Scanner 1 (an X-ray source), as shown in FIG. 2, has an X-ray tube 8 wherein an X-ray is controlled by an X-ray tube control device 7. The X-ray eradiated from the X-ray tube 8 becomes, for example, X-ray beam having a pyramid shape that is cone beam X-ray by a collimator 10 controlled by a collimator control device 9, and is irradiated to the object 17. The X-ray transmitted through the object 17 is inputted to the detector 11.

The detector 11 is arranged facing the X-ray tube 8 having the object 17 therebetween, and is for detecting X-rays and outputting X-ray projection data. More specifically, the detector 11, as shown in FIG. 3, has a plurality of X-ray detection elements 18 two-dimensionally arranged in channel direction and row direction. Configuration of the detector 11 will be described later. A data-collecting device 12 is connected to the detector 11. The data-collecting device 12 is for collecting detection data from the respective discrete X-ray detection elements 18 of the detector 11.

The above-mentioned components from the X-ray control device 7 to the data-collecting device 12 are mounted on a turntable 13 of the scanner 1. The turntable 13 is rotated by driving force propagated from a turntable-driving device 15 controlled by a rotation control device 14 via a driving force propagation system 16. The above-mentioned X-ray detector 11 has configuration wherein the plurality of X-ray detection elements 18 are 2-dimenisonally arranged in channel direction and row direction. The X-ray detection elements 18 configure an X-ray entrance plane curved in cylindrical shape as a whole or broken line form in channel direction, and the channel number "i" is, for example, in the range of 1~1000, and the row number "j" is, for example, in the range of 1~1000. Also, X-ray detection elements 18 are configured by the combination of, for example, scintillator and photodiode. The spread angle of the cone beam X-ray in channel direction which coincides with the array direction of channels in the X-ray detector 11, that is the fan angle is α, and the spread angle of the cone beam X-ray in row direction which coincides with the array direction of the row in the X-ray detector 11, that is the cone angle is γ.

As shown in FIG. 4, after the object 17 laid on the top panel 4 of the patient table 2 is carried in the opening of the scanner 1, upon irradiation of the cone beam X-ray wherein a cone angle γ is adjusted by the opening width of the collimator 10 to the object 17, the image of the object 17 to which the cone beam X-ray is irradiated is projected by the X-ray detector 11, and the X-ray transmitted through the object 17 by the X-ray detector 11 is detected.

The patient table 2 shown in FIG. 2 is configured so that the height of the table is adjusted properly by the control of a patient table control device 20 via a patient table vertical motion device 21, and the object 17 is carried in and out of an X-ray irradiation space of the scanner 1 by moving the top panel 4 back and forth by controlling a top panel driving device 22 through the patient table control device 20.

The console 3 shown in FIG. 2 has a system control device 19. The scanner 1 and the patient table 2 are connected to the system control device 19.

More specifically, the X-ray control device 7, the collimator control device 9, the data collecting device 12 and the rotation control device 14 in the scanner 1 are controlled by the system control device 19. Also, the patient table control device 20 in the patient table 2 is under control of the system control device 19.

The data collected by the data collecting device 12 in the scanner 1 is inputted to an image reconstruction device 23 by the control of the system control device 19.

The image reconstruction device 23 constructs a scanogram image using the scanogram projection data (object perspective data) collected by the data collecting device 12 upon scanogram imaging, and reconstructs a tomographic image based on the X-ray projection data from the plurality of views collected by the data collecting device 12 upon scanning.

Scanogram images constructed or tomographic images reconstructed in image reconstruction device 23, variety of data, and program for carrying out the function of the X-ray CT apparatus are stored in a storage device 24 connected to the system control device 19.

The display device 5 and the operation device 6 are also connected to the system control device 19 respectively. Display device 5 displays the reconstructed images outputted from the image reconstruction device 23 or various sorts of information that the system control device 19 deals with.

The operation device 6 is to be operated by the operator, and is for executing the input operation of the various sorts of commands or information by the operator and input processing of the commands or information to the system control device 19. For example, the operation device 6 carries out the input operation of the desired image quality index value to be described later, with respect to a tomographic image obtained by the image reconstruction device 23. The operator interactively operates the present X-ray CT device 50 using the display device 5 and the operation device 6.

The system control device 19 is also connected with a scan-planning device 25, and is capable of setting conditions for scanning in advance using commands inputted through the operation device 6 by the operator and scanogram images read out from the storage device 24, and creating a scanning plan. More specifically, a scanogram image read out from the storage device 24 is displayed on display device 5, and it is possible to plan a slice position by specifying the coordinate of the position to which the tomographic image is reconstructed (hereinafter, referred to as a slice position) using the operation device 6 being operated by the operator on the displayed scanogram image of an object.

Furthermore, the information of the planned slice position is stored in the storage device 24, and is used also for planning X-ray dose control condition, etc. by scan-planning device 25.

In the X-ray CT device 50 of the present invention, various sorts of preparation operation are carried out for setting image condition, before the scanning for obtaining a tomographic image of the object. As for the preparation operation, processing such as generation of a scanogram image for setting a slice position of the object, data analysis of the generated scanogram image, determination of the most appropriate X-ray irradiation dose modulation pattern based on the scanogram projection data, construction and display of the simulated image upon using/not using the X-ray dose optimization function are performed under the control of the system control device 19.

Particularly, analysis of the scanogram data, determination of the best suited X-ray irradiation dose modulation pattern as the imaging condition based on the analyzed data, construction and display of the comparative simulated image upon using and not using the X-ray dose optimization function are significant functions of the scan-planning device 25 connected to the system control device 19.

Main components engaged with these preparation operations are devices such as the system control device 19, the scan-planning device 25, the operation device 6, the display device 5, the X-ray tube 8 and the detector 11.

In these preparation operations, the operator first input mainly the X-ray conditions such as X-ray tube voltage (tube voltage) and a setting value of the X-ray tube current (tube current) to the system control device 19 using the input device 6.

The X-ray tube 8 and the detector 11 perform the scanogram imaging by relatively moving the table 2 and the turntable 13 along the body axis of the object 17 without rotating the turntable 13, and store the scanogram projection data and scanogram image data to the storage device 24.

The scan-planning device 25 analyzes the scanogram projection data, and makes an supposed cross-section in the arbitrary position along the body axis of the object into, for example, a model as a cross-section which is similar to an applicable region of a standard human body model (for example, a male adult with 173 cm height and 65 kg weight). The standard human model has X-ray projection data (standard X-ray projection data).

Accordingly, a 3-dimensional model (hereinafter, referred to as an object 3-dimensional model) is generated which varies its form and CT value distribution depending on the position along the body axis of the object (hereinafter, referred to as z-position). Data of the standard human model and the object 3-dimensional model are stored in the storage device 24.

The scan-planning device 25 calculates a sequence of tube current value that varies over time according to the variation of the transmission X-ray dose supposed in the imaging region of the object, that is modulation pattern of the tube current, based on the desired image quality index value, tube voltage, tube current setting value, X-ray collimation condition, time per one rotation of scanning (hereinafter referred to as scanning time) inputted from the operation device 6, and data of the object 3-dimensional model created by the scan-planning device 25.

Furthermore, scan-planning device 25 creates data such as graphs for comparing the simulated images or image index values in case of using and not using the X-ray dose optimization function respectively, and displays them for comparison on the display device 5 via the system control device 19.

<Flow of the Preparation Operation Process>

FIG. 5 is a program block diagram related to the preparation operation. The program related to the preparation operation is configured by the input unit 24a, the scanogram data reading unit 24b, the model generation unit 24c, the optimization unit 24d, the image construction unit 24e, the display unit 24f and the comparative information generating unit 24g. The details of the respective programs will be described later.

A flow chart of a sequence of the preparation operation prior to the scanning in the X-ray CT apparatus 50 is illustrated in FIG. 6. The scan-planning device 25 reads out from the storage device 24 and executes the above-mentioned program related to the preparation operation in the flow of the preparation operation.

While image SD value, contrast-noise comparison (CNR), an identifiable radius under a predetermined CNR (a radius of an identifiable abnormal shadow) and signal-noise ratio (SNR) can be cited as the image quality index value, the case of image SD value will be exemplified below.

(Step S100)

In the scanogram imaging in step S100, scanogram imaging of the object 17 is performed, and a scanogram image is generated (S100). The generated scanogram image is stored in the storage device 24.

The procedure for generating a scanogram image of the object 17 by the scanogram imaging and the procedure for reconstructing a tomographic image by scanning are basically the same. Scanogram projection data can be acquired by irradiating X-ray unidirectionally, for example, from back direction, with respect to the object 17, without rotating the turntable 13, and loading the X-ray projection data (detection data) by the detector 11.

The X-ray projection data (scanogram projection data) obtained by the scanogram imaging is transmitted from the detector 11 to the image reconstruction device 23 via the system control device 19, and the scanogram image is generated in the image reconstruction device 23.

The generated scanogram image is viewed unidirectionally, for example, an image constructed by X-rays being transmitted from the backside to the front side is viewed from the front direction.

This scanogram image is used for setting the slice position of the object 17 upon scanning (position for reconstructing a tomographic image). Also, the scanogram projection data is used not only for generating scanogram images, but in particular in the present invention for determining the modulation pattern of the X-ray irradiation dose (scan dose) upon scanning, and also for generating an image using/not using the X-ray dose optimization function (simulated images for comparison) or creating information such as graphs indicating the variation of the image quality index value. The slice position is represented as the above-mentioned Z-position.

(Step S110~Step S130)

In step S110~step S130, the operator inputs the top panel movement pitch (S110), scanning start position (S120), and scanning end position (S130) as scanning condition, using input device 6 referring to the scanogram image. Using these input data, by the scan-planning device 25, the imaging range in body axis direction of the tomographic image of the object 17, Z-position (slice position) and the phase angle (phase angle of the turntable 13) $\beta$ of the X-ray tube 8 are determined. Here, the scanning start position and the scanning end position means the Z-position of the first tomographic image and the Z-position of the last tomographic image obtained respectively in the sequence of scanning.

(Step S140)

In step S140, the operator inputs data such as the tube voltage setting value, scanning time, X-ray collimation condition, kind of the reconstructing filter and view range from the input device 6 as the imaging condition (S140).

(Step S150)

In step S150, the operator carries out the operation for inputting a desired value as the image quality target (the value indicating the desired image quality) with respect to the image quality index value by the operation device 6 (S150). The input device 24a receives the input of the desired value to the scan-planning device 25.

(Step S160)

In the scanogram projection data analysis of step S160, the scanogram data reading unit 24b reads out the scanogram projection data from the storage device 24, and the scan-planning device 25 analyses the scanogram projection data (S160).

(Step S170)

In the 3-dimensional model generation of the object in step S170, the model generating unit 24c generates the 3-dimenisonal model of the object based on the data of the standard human body model in the storage device 24 (S170).

The 3-dimensional model of the object is a model wherein the respective cross-sections of the object 17 corresponding to the z-position are approximated as having the cross-sections similar to the relevant regions of the standard human model (object cross-section model).

As for the method for approximating a cross-section of the object 17 by a similarity transformation from the standard human body model, known methods are disclosed such as the Patent Document JP-A-2002-263097. The model generating unit 24c generates a 3-dimensional model of the object by generating the object cross-section model in the body axis direction from the scanogram data.

(Step S180)

In step S180, the optimization unit 24 calculates the z-position and X-ray attenuation exponent T with respect to every phase angle $\beta$ of the X-ray tube 8 (S180).

Here, the X-ray attenuation exponent T represents the integral value of the X-ray absorption coefficient distribution along the X-ray transmission path passing the center of the elliptic cross section in the (z, $\beta$) of the object 3-dimensional model. Since the X-ray attenuation exponent T can be obtained from the object 3-dimensional model generated in S170, the scan-planning device 25 calculates it by calling up the object 3-dimensional model from the storage device 24. The calculation result related to the X-ray attenuation exponent T is represented as T=T(z, $\beta$)

(Step S190)

In step S190, the optimization unit 24d converts the function of X-ray attenuation exponent T, from T=T(z, $\beta$) to the function T=T(t) of the time "t", based on the scanning start position, scanning end position, top panel moving pitch and scanning time (S190).

(Step S200)

In step S200, the optimization unit 24d calculates the tube current modulation pattern I(t) represented by the function of scanning time "t" (S200).

Here, the view number to be used for reconstructing the tomographic image Img(z) in the z-position (slice position) is represented as M, and the politic view number "m" is set as: m=0~M−1. When the view number for one rotation is set as N, the view number M for use is not necessarily the same as the view number N for one rotation.

Here, the aforementioned X-ray attenuation exponent T can be also represented as the function T (m) of the view number to be used. In the case that the maximum value of the X-ray attenuation exponent T in the view number m=0~M−1 is set as Tmax (0:M−1) and it is supposed that the reference tube current value i_ref is to be corresponded to the set Tmax (0:M−1) at that time, the tube current value $i_v(m)$ with respect to the view number "m" is to be as the following formula:

$$i_v(m)=i\_ref*\exp(T(m)-T\max(0{:}M-1)).$$  [Formula 1]

On the other hand, the image noise distribution value V is expressed as the following formula as the function of the X-ray attenuation exponent T, in the case that the time "trot" for one rotation of the scanner equals the reference time trot_ref, the X-ray attenuation exponent T is a steady value during that time, "xv" is used for the tube voltage, the reference tube current value i_ref is used for the tube current value "i", uniform weighting is performed on the view number N_ref during one rotation, the reconstruction filter function "g" is used and the image thickness "thk" is reconstructed as the reference image thickness thk_ref.

$$V(T,i\_ref,trot\_ref,thk\_ref)= c(xv,g,i\_ref,trot\_ref,thk\_ref)*\exp(a(xv)*T)$$  [Formula 2]

However, a(xv) is a fixed number depending on the tube voltage xv, $$c(xv, g, i, trot, thk) = \frac{b(xv, g) * i\_ref * trot\_ref * thk\_ref}{i * trot * thk},$$

b(xv,g) is a fixed number depending on the tube voltage "xv" and the reconstruction filter function "g", and a(xv), b(xv,g) are stored in the storage device 24 in advance.

The image noise distribution estimated value V* in the case of using the tube current value $i_v(m)$ expressed in the above-mentioned formula 1 is to be expressed as the following formula:

$$V^* = N * \sum_{m=0}^{M-1} \left( w(m) \bigg/ \sum_{m=0}^{M-1} w(m) \right)^2 * V(T(m), i_v(m), trot, thk) \quad \text{[Formula 3]}$$

Here, w(m) in the formula 3 is the view direction weight to be applied with respect to each view "m". The view direction weight is used for the case that the view number M to use for the reconstruction and the view number N for one rotation are different, or the case of correcting artifacts due to the movement of the object (G. Wang et al. "Half-Scan Cone-Beam X-ray Microtomography Formula" Journal of Scanning Microscopies Vol. 16, 216-220 (1994), JP-A-H08-280664).

Additionally, in the case that the view number M for use equals the view number N for one rotation, so-called "full scan reconstruction" can be performed by setting:

$$w(m)=1 \; (m=0{\sim}N-1). \quad \text{[Formula 4]}$$

Here, based on the desired image noise distribution value $V_{tgt}$ (the square value of $SD_{tgt}$) set by the desired value $SD_{tgt}$ of the image SD value inputted by the operator and the image noise distribution estimated value V* of formula 3, the tube current value $i_a(m)$ to be actually applied is set as the following formula:

$$i_a(m) = i_v(m) * \frac{V^*}{V_{tgt}} \quad \text{[Formula 5]}$$

As described above, it is possible to determine the tube current modulation pattern for attaining the desired value of the image SD value inputted by the operator on the tomographic image of each z-position (slice position). When thus determined tube current modulation pattern is set as "I", "I" can be expressed as the function I(t) of the elapsed time "t" after the start of the scanning time.

More specifically, in the present step, by setting an irradiation dose standard modulation curve ($i_v(m)$) which changes the dose of X-ray irradiation being irradiated from the X-ray tube 8 based on the object cross section model with respect to every view and correcting the irradiation dose standard modulation curve ($i_v(m)$) based on the comparison between the standard image noise distribution value V* in the case of irradiating the X-ray dose corresponding to the set irradiation target modulation curve ($i_v(m)$) and the desired image noise distribution value $V_{tgt}$ set from the desired value (image $SD_{tgt}$) the optimization unit 24d determines the irradiation dose modulation curve ($i_a(m)$) which indicates the optimized X-ray irradiation dose for attaining the desired value and modulate the X-ray irradiation dose based on the determined irradiation modulation curve ($i_a(m)$).

Such determined tube current modulation pattern I=I(t) is stored in the storage device 24, sequentially called up by the system control device 19 upon scanning in accordance with the imaging region of the object 17, and controls the tube current during scanning via the X-ray control device 7.

(Step S210~S230)

Next, generation and display of the simulated image for image quality comparison in steps S210~S230 will be described. FIG. 7 shows the generation procedure of the simulated image. As for the simulated image, other than an MPR image, a 3-dimensional display image or a cross-sectional image may be used. Here, MPR image (Multi Planer Reconstruction image) is used as the simulated image.

In step S210, the image generation unit 24e reads out the standard human body scanogram image 26 and the scanogram image 27 of the object 17 from the storage device 24. Then the image generation unit 24e obtains the scale of enlargement M for converting the standard human body scanogram image 26 into the same size as the scanogram image 27 of the object 17 (S210).

FIG. 7 (a) shows the procedure for calculating the scale of enlargement M. The scale of enlargement M is obtained using the information such as shape of the corresponding region of both images. For example, when the length from the upper end of the rib bone to the lower end is set as the corresponding region and a corresponding region A of the standard human body scanogram image 26 and the corresponding region B of the scanogram image 27 of the object 17 are used, the scale of enlargement M is obtained as M=B/A.

In step S220, the image construction unit 24e constructs the object simulation MPR image 29 without noise which is a simulated image of the object 17 by multiplying the standard human body MPR image 28 based on the standard human body model shown in FIG. 7(b) by the scale of enlargement M (S220).

Here, since the standard human model presents the CT value distribution (standard X-ray projection data) of the standard human body, the fact that the appropriate cross-section diagram of the standard human body model is equivalent to the standard human body MPR image 28 is utilized for construction of the object simulation MPR image 29. Since there is no noise in the standard human body model, no image noise will be found also in the standard body MPR image 28 and the object simulation MPR image 29. Hereinafter, the standard human body MPR image 28 and the object simulation MPR image 29 without noise is referred to as an MPR image 28 and an MPR image 29 respectively.

In step S230, the scan-planning device 25 (image generation unit 24e) calculates the image noise (estimated noise) estimated in the each case of using and not using the X-ray dose optimization, and generates the simulated image (MPR image) by adding the calculated image noise to the MPR image 29. Here, the case of not using the X-ray dose optimization means that the rotation scanning is performed using the X-ray tube current value set by the operator in all of the views or by the standard X-ray tube current value. In other words, the imaging is performed without being modulated for each view, by a fixed tube current and the same X-ray irradiation dose from any view around the object, in all z-positions of the imaging range.

FIG. 7(c) shows the MPR images 30 and 31 generated by the image generation unit 24e. In the diagram, the image noise is indicated by dots. The image generation unit 24e generates two kinds of the simulated images (MPR images) below. One is the object simulation MPR image 30 with noise (the supposed image without using the optimization supposed to be obtained when the rotational imaging is performed without modulating the X-ray irradiation dose based on the irradiation modulation curve) being supposed in the case of not using the X-ray dose optimization function. The other one is the object simulation MPR image 31 with noise (the supposed image using the optimization supposed to be obtained when the rotational imaging is performed by modulating the X-ray irradiation dose based on the irradiation modulation curve) being supposed to be obtained in the case of using the X-ray dose optimization function.

The region 31a in the MPR image 31 has more increased noise than the region 30a in the MPR image 30, thus there is a case that the noise is partially increased when the X-ray dose optimization function is used. However, uniformity of noise as the entire image is improved. Therefore, the uniformity of the image quality is also improved by the X-ray dose optimization function.

FIG. 8 shows an image display example wherein the MPR images 30 and 31 and the image index value comparison graph 32 are juxtaposed and displayed. The display unit 24f comparatively displays (an image comparison display) the MPR images 30 and 31 on the same screen of the display device 6.

The image generation unit 24e may create an image index value comparison graph 32 indicating comparison of the fluctuation, along the z-position, between the image quality index values (image SD values) supposed to be obtained in the case of using and not using the X-ray dose optimization, that is between the image quality index values corresponding to the X-ray dose standard modulation curve and the image quality index values corresponding to the optimized irradiation dose modulation curve. The lateral axis of the image index value comparison graph 32 indicates the image SD value, and the vertical axis indicates the z-position. In the image index value comparison graph 32 of FIG. 8, the dotted line (not using the X-ray dose optimization) indicates the fluctuation of the image SD value in the case of not using the X-ray dose optimization function, and the solid line (using the X-ray dose optimization) indicates the fluctuation of the image SD value in the case of using the X-ray dose optimization function.

The image quality index value comparison graph 32 makes it possible to grasp the fluctuation of the image SD value quantitatively, and to easily compare the image quality in the case of using and not using the X-ray dose optimization function.

The display device 5 may place the MPR images 30, 31 and the image quality index value comparison graph 32 side by side on a screen, or display only the image quality index value comparison graph 32 (S230).

(S240)

In the image determination of step S240, determination is made whether the effect of the X-ray dose optimization is appropriate or not, by the operator observing the image quality comparison display (using/not using the X-ray dose optimization function, that is the MPR images 30 and 31) of the object in step S230 (S240).

When the operator determined that the image quality is optimum the scanning preparation operation is ended and the scanning is started, and when it is determined that the image is not optimum the step is returned to step S150 and the desired image quality index value is inputted again.

In accordance with the present embodiment, it is possible to suppose the appropriate image quality in advance and to perform the optimum scanning to achieve the supposed image quality, by determining the suitable X-ray irradiation dose modulation pattern through inputting the desired value of the image quality index value prior to the X-ray CT scanning and comparing the supposed image quality in each case of using and not using the X-ray dose optimization.

As described above, in the X-ray CT apparatus 50 related to the present invention, the scan-planning device 25 can generate a 3-dimensional model of the object 17 from the scanogram projection data of the object 17. Also, scan-planning device 25 can suppose the image noise according to the imaging region of the object from the 3-dimensional model of the object 17, and to automatically set the modulation pattern of the X-ray irradiation dose (scan dose) (X-ray dose optimization) from the comparison between the supposed image noise and the desired value of the image quality index value inputted by the operator. Furthermore, scan-planning device 25 can suppose the image in each case of using and not using the X-ray dose optimization function, and comparatively display the simulation images reflecting the image quality of the respective cases on the display device 5.

Accordingly, it is possible to concretely and easily grasp, prior to the actual scanning, the effect to be attained by the X-ray dose optimization function which influences the image quality, and to easily perform the X-ray CT examination for obtaining an image of the object with optimum image quality.

The image generation unit 24d may generate the chart indicating the image quality index value (image SD value) supposed to be obtained in each case of using/not using the X-ray dose optimization, and display the generated chart on the display unit 24f.

Also, while the tube current is modulated above for optimizing the scan dose, the tube voltage may be modulated.

THE SECOND EMBODIMENT

In the present embodiment, in step S145 of the first embodiment, the target region is particularly specified, and the image comparison is performed regarding the target region by a comparative-information generating unit 24g. FIG. 9 is a flow chart showing the flow of the preparation operation related to the present embodiment. The steps similar to FIG. 5 are indicated in the same step numbers.

(Step S100~Step S140)

In steps S100~step S140, in the same manner as the first embodiment, the scanogram imaging is performed (S100) and the scanning condition is inputted (S110~S140).

(Step S145)

In step S145, the operator specifies the target region on the scanogram image 27 of the object 17 by the operation device 6 (S145).

(Step S150~S220)

In steps S150~S220, in the same manner as the first embodiment, the operator inputs the desired value with respect to the image quality index value (image quality SD value) (S150).

Furthermore, the scanogram data is analyzed (S160), the object 3-dimensional model is generated (S170), the X-ray attenuation index T and the tube current modulation pattern are calculated (S180, S190, S200) and the simulated image (MPR image, etc.) of the object is generated (S210, S220).

(Step S230)

In step S230, the comparative information generating unit 24g generates the comparative information for comparing the information of the target region in the supposed image using optimization (MPR image 31) and the information of the target region in the supposed image without using the optimization (MPR image 30). Also, display unit 24f displays the information regarding the supposed image quality in each case of using and not using the X-ray dose optimization function (comparative information) (S230). The position equivalent to the target region in the simulated image (MPR images 30 and 31) is reflected in the display in the present step.

The comparative information generating unit 24g may generate the information indicating the position of the target region in the supposed image using optimization (MPR image 31) and the supposed image without using optimization (MPR image 30), or the image quality index comparison graph 32 for indicating the image quality index value of the target region, as the comparative information.

FIG. 10 shows the image display example on which the comparative display of the image quality and the target region are combined and displayed. On the MPR images 30, 31 and the image quality index comparison graph 32, a display frame 33 for displaying the position equivalent to the target region is indicated. In FIG. 10, MPR images 30, 31 and the image quality index comparison graph 32 are juxtaposed and displayed.

In the case that the range of the target region is narrow, comparison of the numeric value of the concrete image quality index value (image SD value) is also useful. The image generation unit 24e may generate a numeric value comparative chart containing the numeric value information indicating the image quality index value (image SD value) of the target region in the supposed image using optimization (MPR image 31) and the supposed image without using optimization (MPR image 30).

FIG. 11 shows the image display example of the numeric value comparative chart 34 displayed by the display unit 5. In the numeric value comparative chart 34 of FIG. 11, the measurement of the tube current (tube current) in the target region and the estimated value of CTDI (Computed Tomography Dose Index) image SD value (image SD estimated value) are displayed in each case of using and not using the X-ray dose optimization function. Accordingly, the image quality can be grasped quantitatively.

(Step S240)

In step S240, in the same manner as the first embodiment, the operator determines whether the effect of the X-ray dose optimization is appropriate or not.

In accordance with the present embodiment, it is possible to concretely and easily grasp the effectiveness for each case of using and not using the X-ray dose optimization function in the target region.

While the specification of the target region is performed above on a scanogram image, it may be performed on one of the MPR images 30 or 31. Also, the position of the target region specified on one of the images is reflected on the other image, and the position equivalent to the target region is also to be displayed on the other image. Also, as for a marker for indicating the position equivalent to the target region on the image, an arrow may be used other than the display pane 33. While the X-ray CT apparatus of the gantry type is described in the embodiment above, the X-ray CT apparatus of the C-arm type may also be used.

BRIEF DESCRIPTION OF THE DIAGRAMS

FIG. 11 is an image display example of a numeric comparative chart.

DESCRIPTION OF THE SYMBOLS

Figure 1:
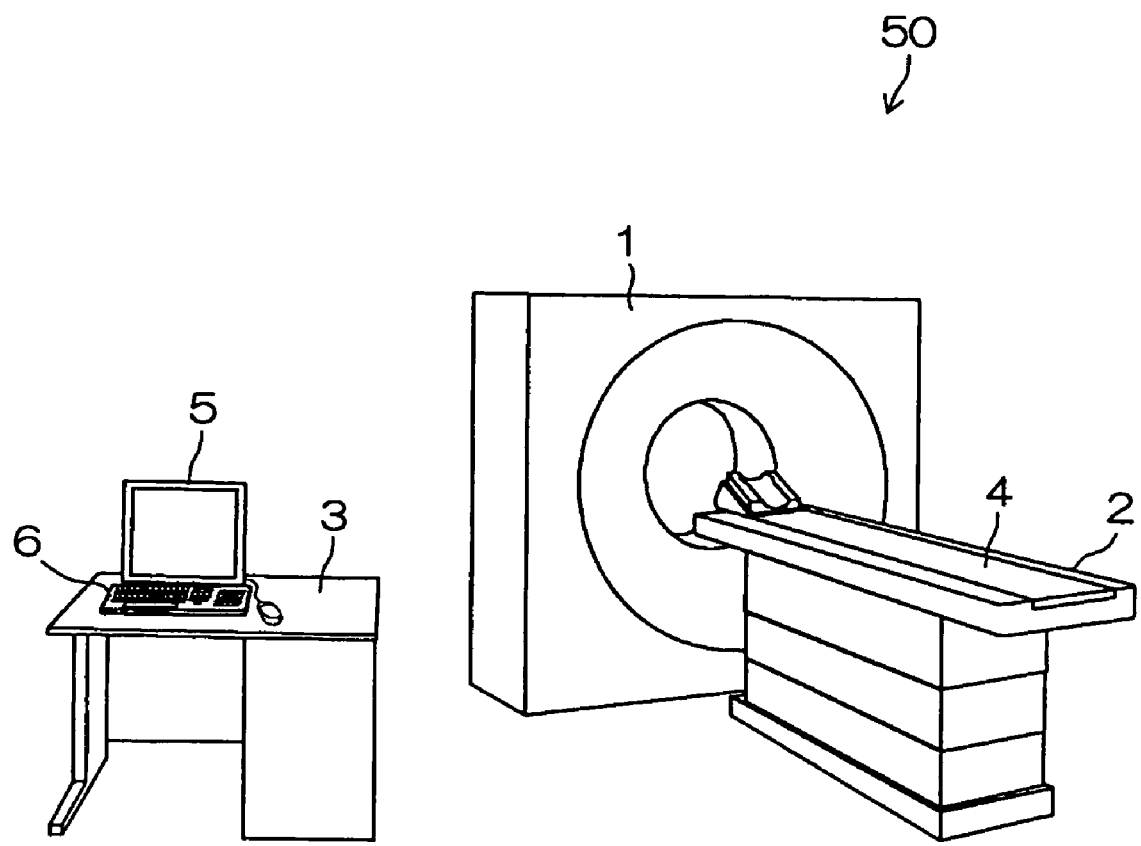
FIG. 1 shows a general overview of the X-ray CT apparatus.
Figure 2:
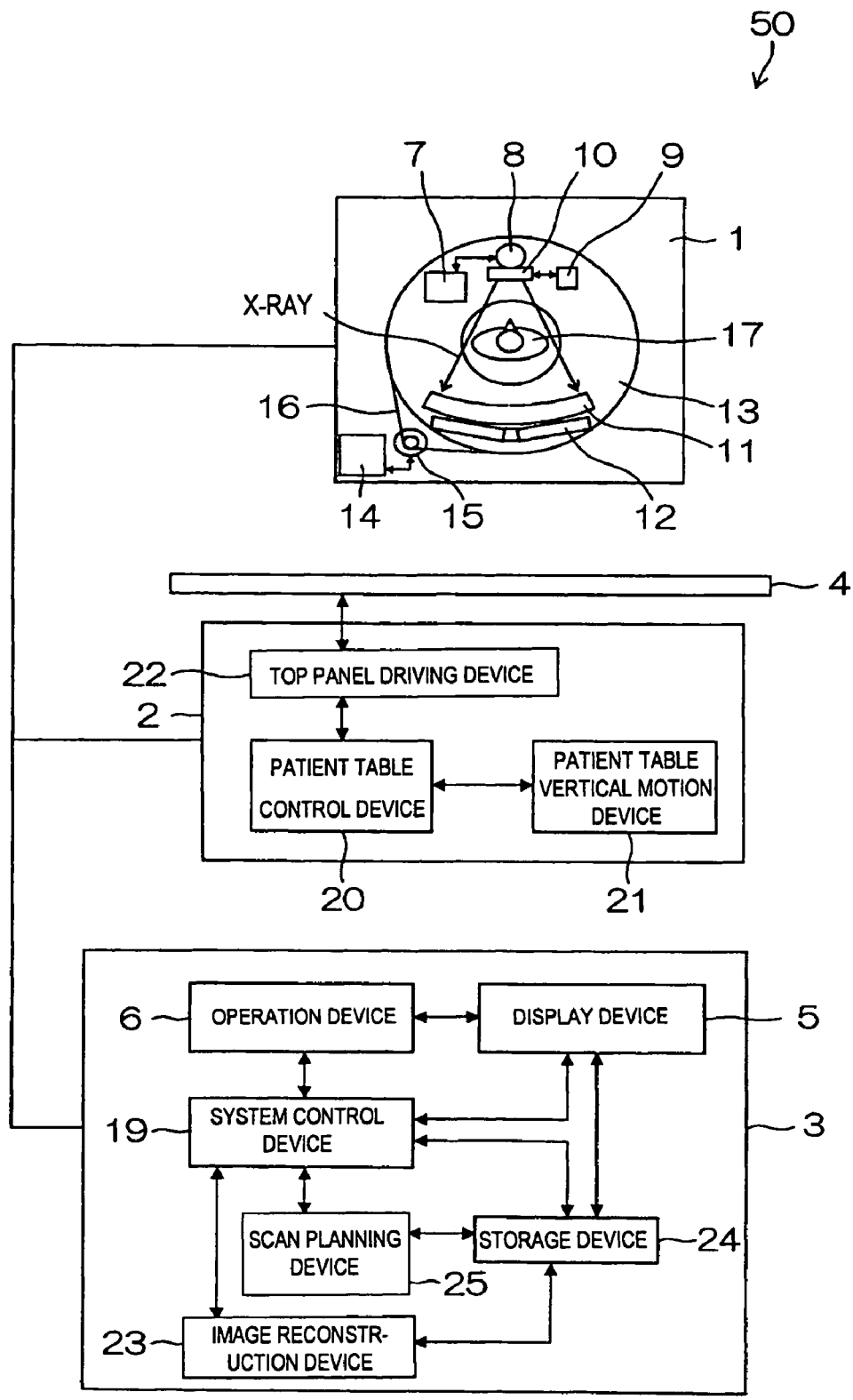
FIG. 2 shows the general configuration diagram of the X-ray CT apparatus.
Figure 3:
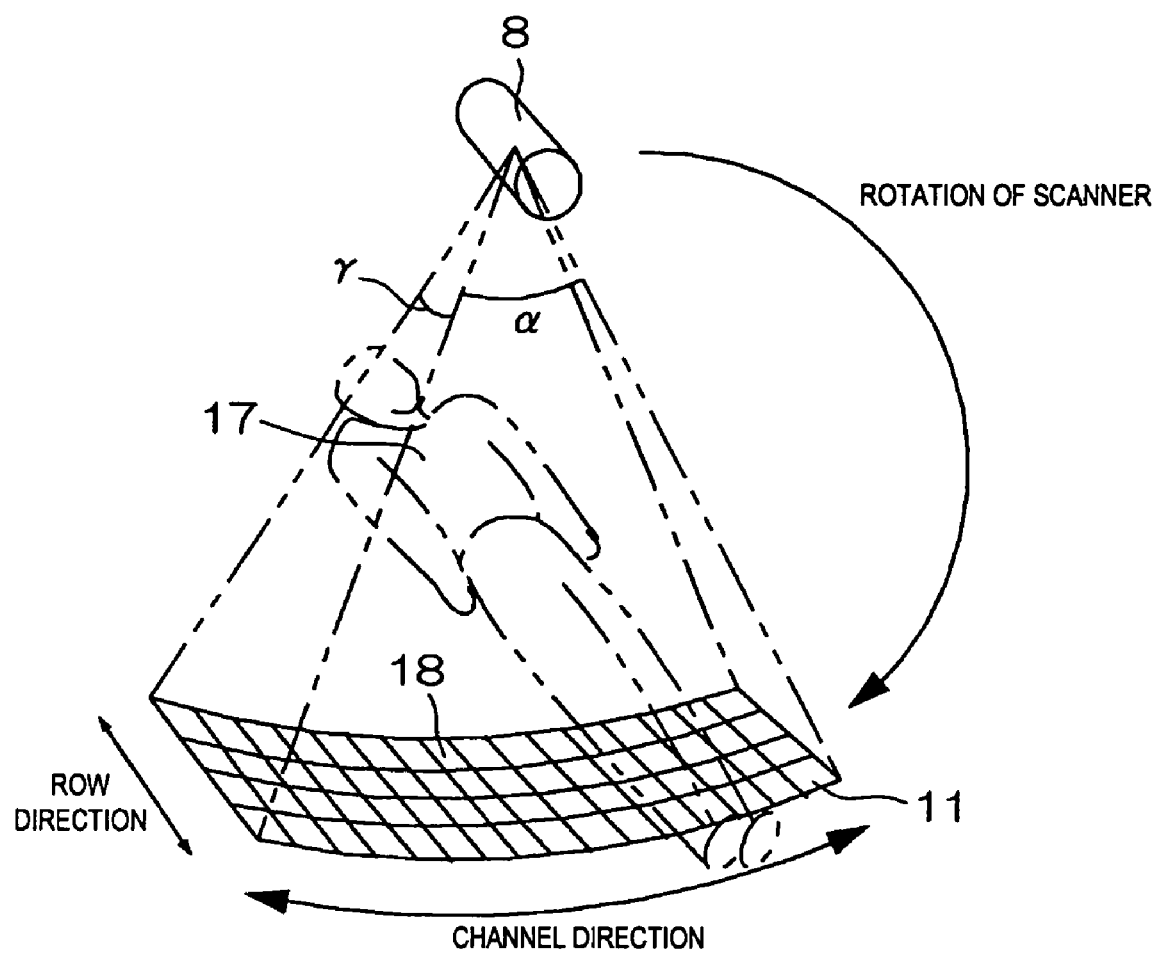
FIG. 3 is a pattern diagram showing configuration of a detector of the X-ray CT apparatus and its relationship with X-ray irradiation.
Figure 4:
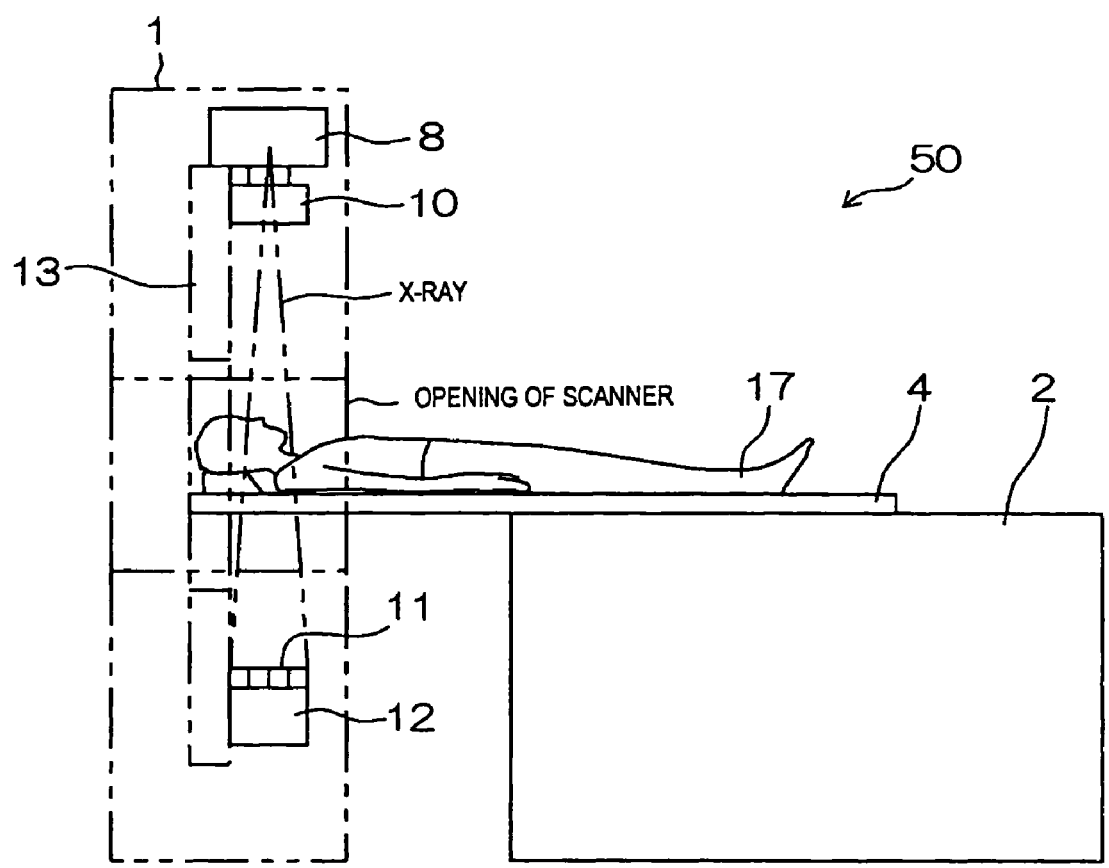
FIG. 4 shows the relationship among an object to be examined, a scanner and a patient table of the X-ray CT apparatus, from lateral direction.
Figure 5:
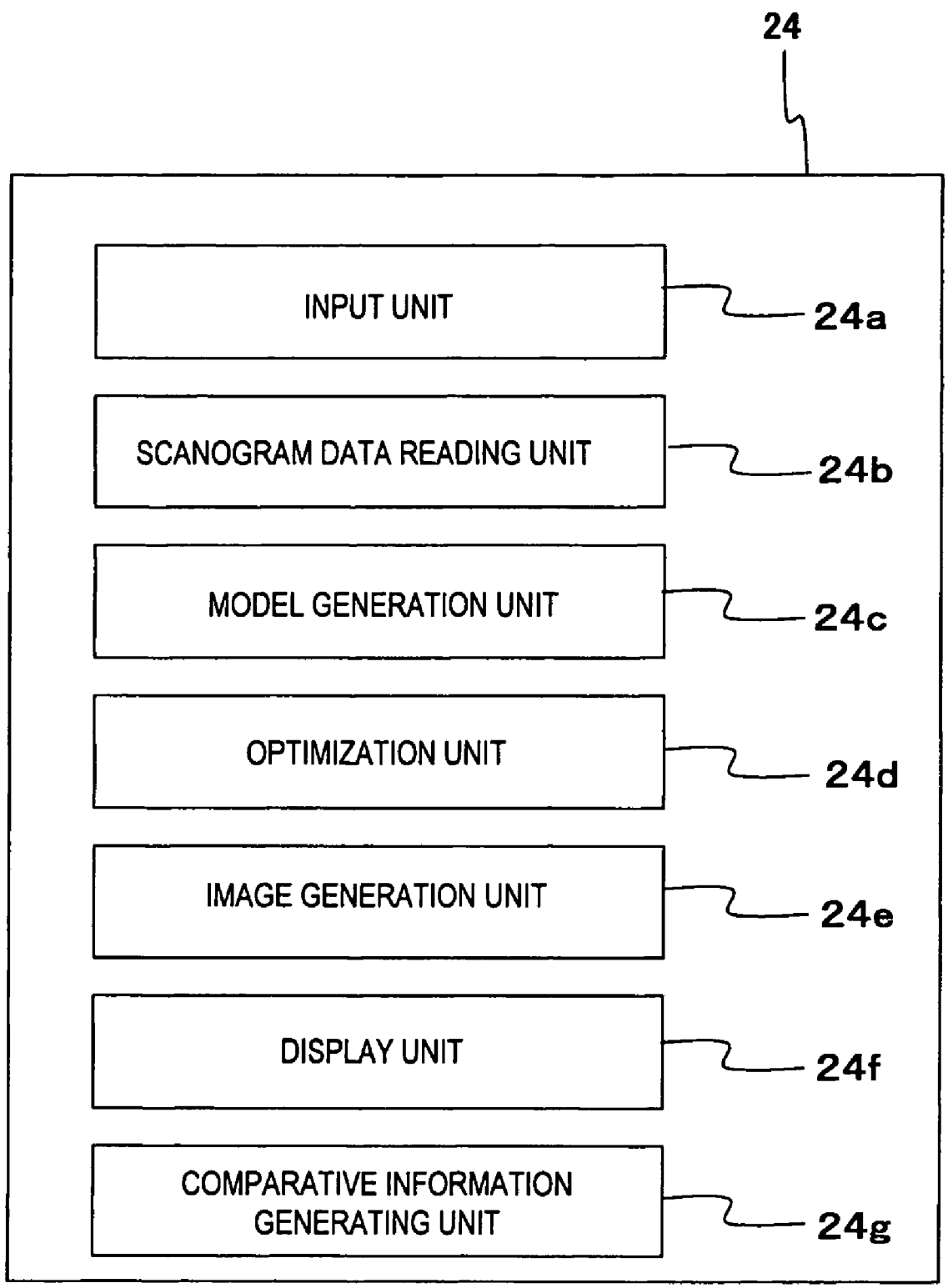
FIG. 5 is a program block diagram regarding the preparation operation.
Figure 6:
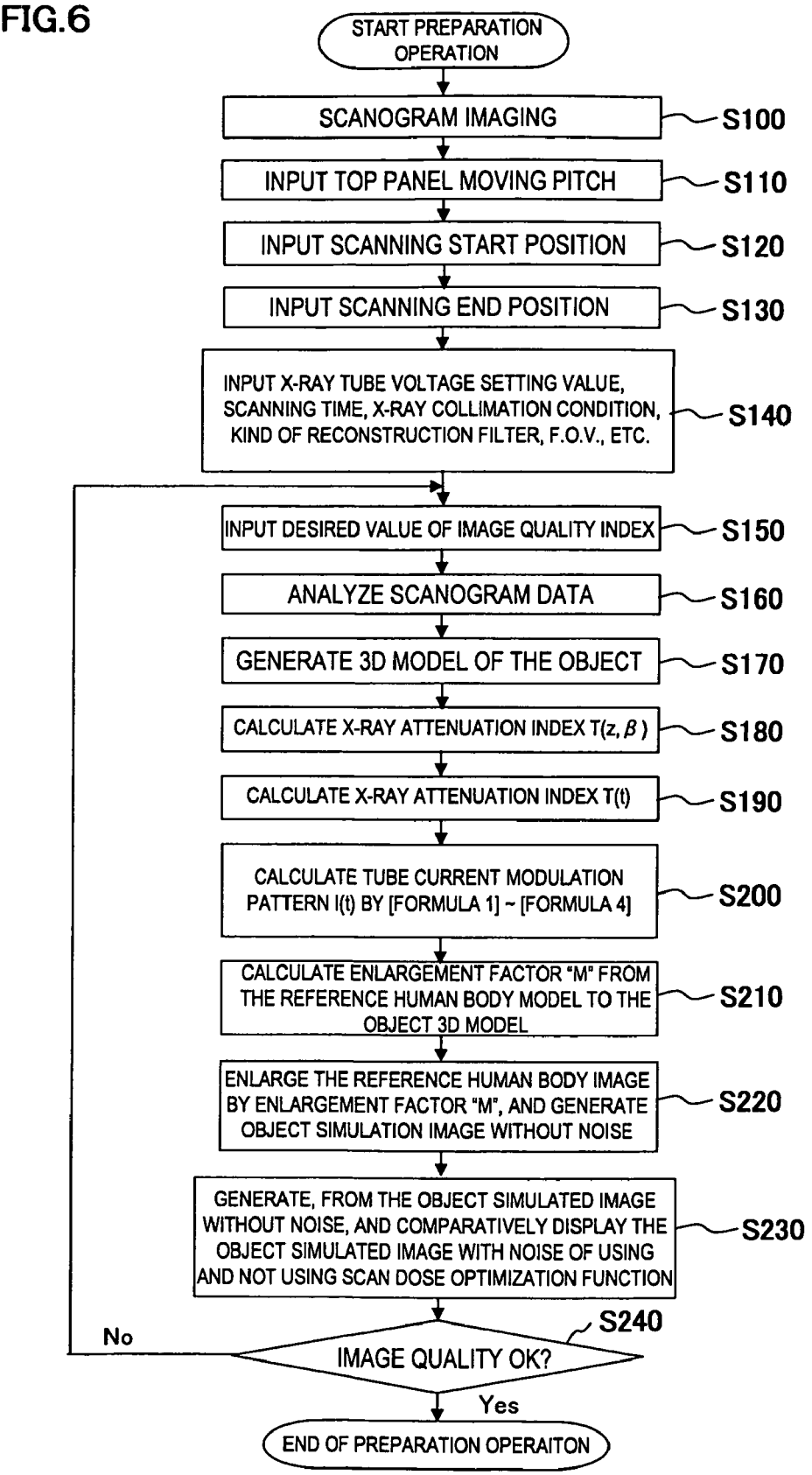
FIG. 6 is a flow chart showing the flow of the preparation operation prior to the scanning, related to the X-ray CT apparatus.
Figure 7:
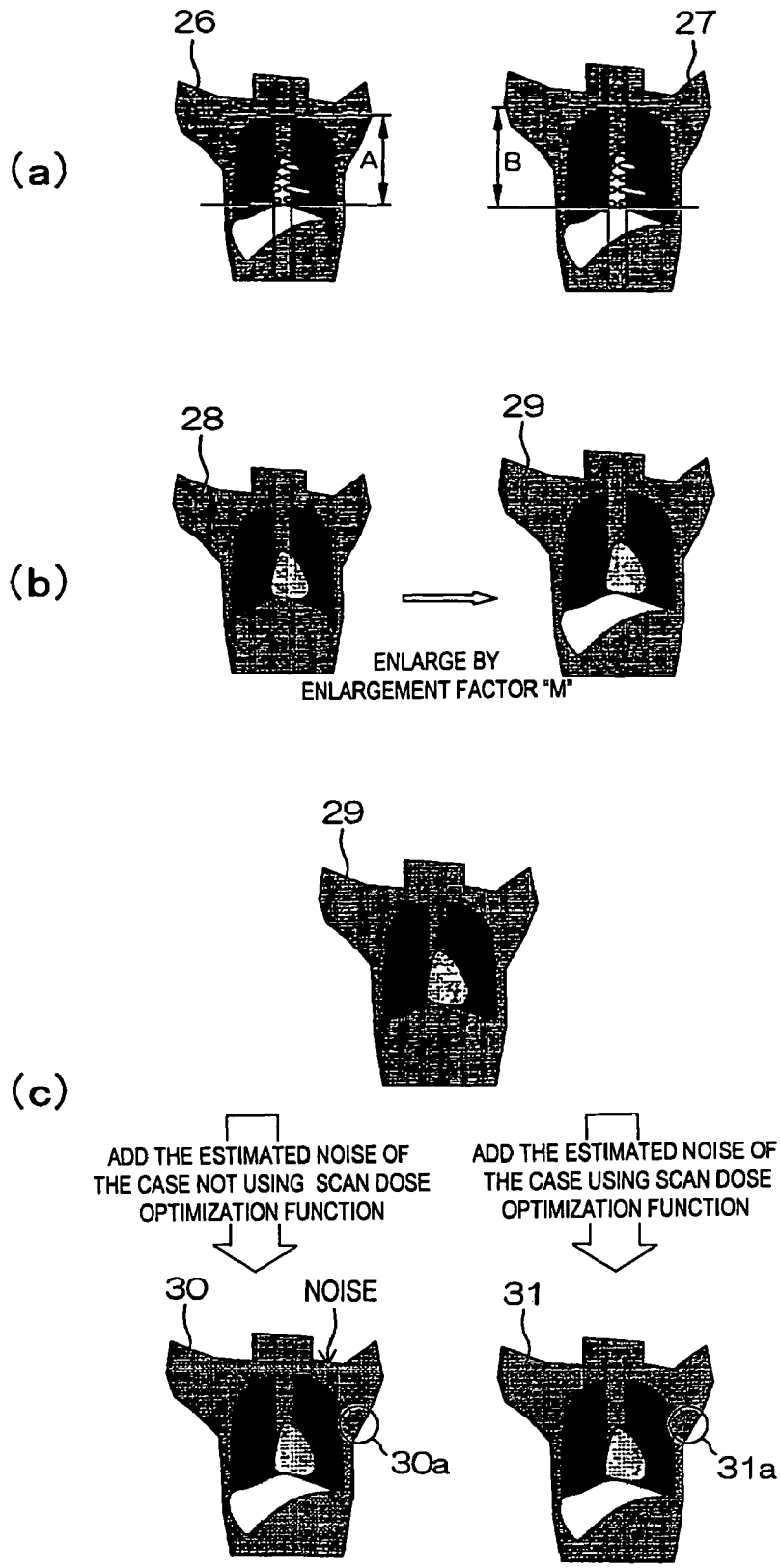
FIG. 7 shows the construction procedure of the simulated images for comparison.
Figure 8:
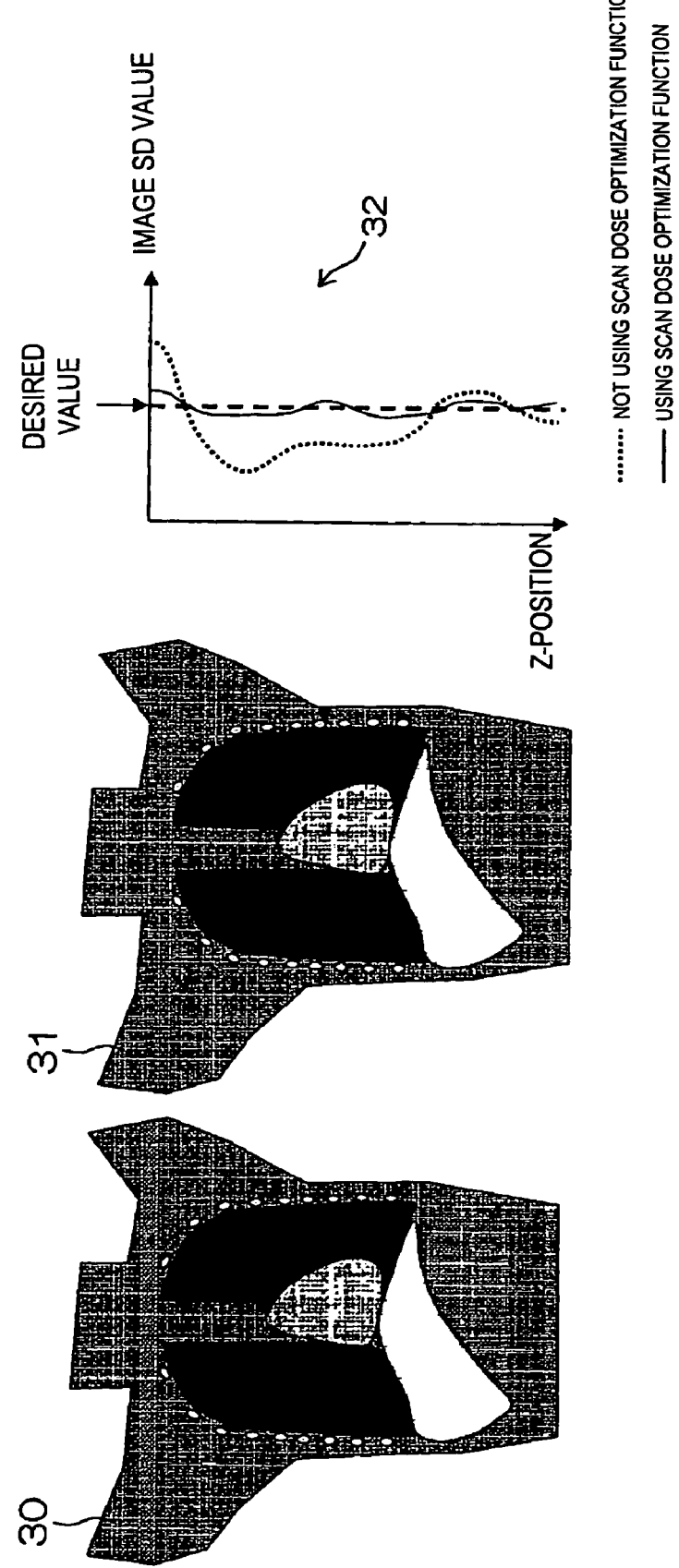
FIG. 8 shows the image display example related to the image comparative display.
Figure 9:
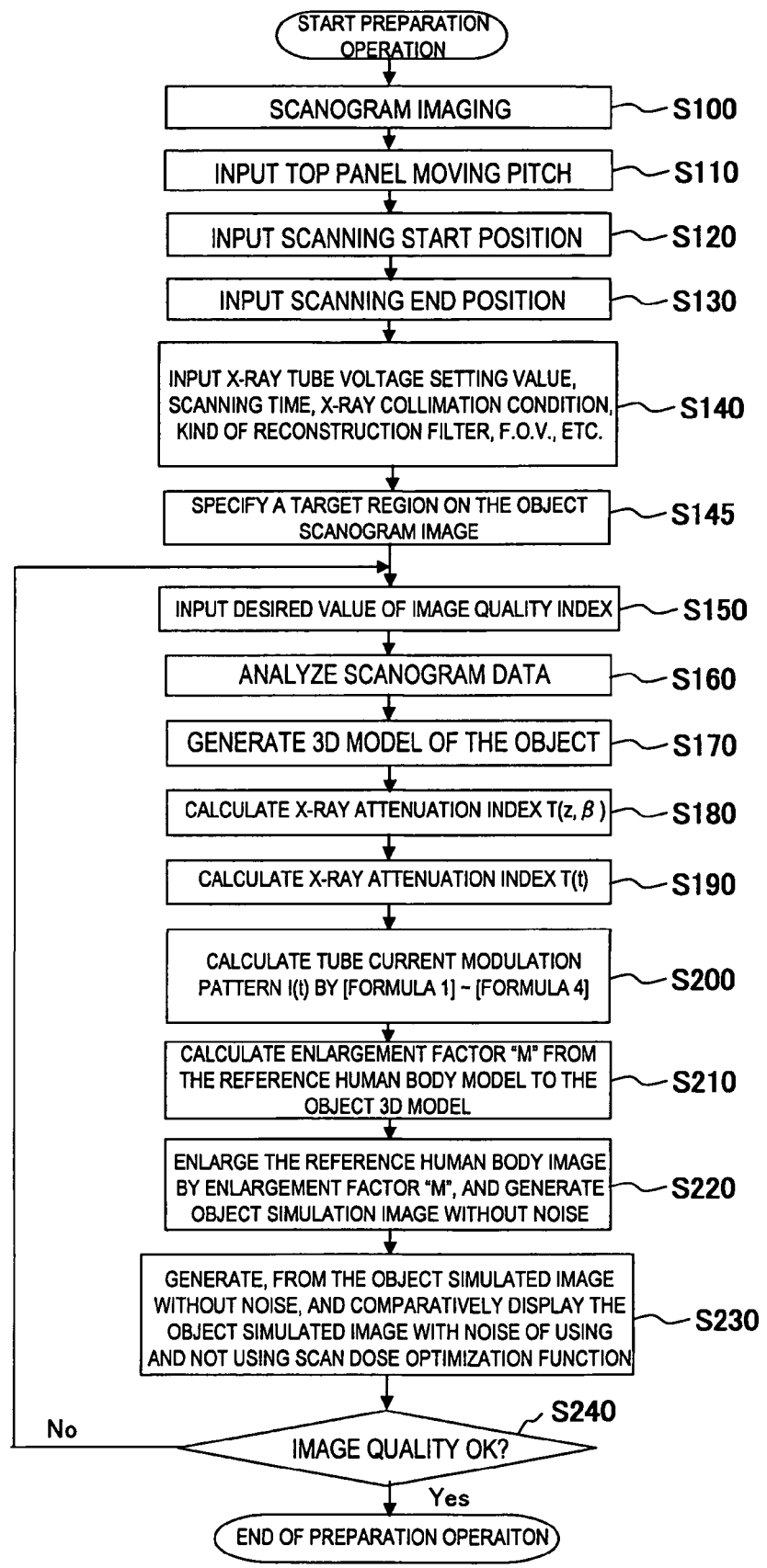
FIG. 9 is a flow chart showing the flow of the preparation operation related to the second embodiment.
Figure 10:
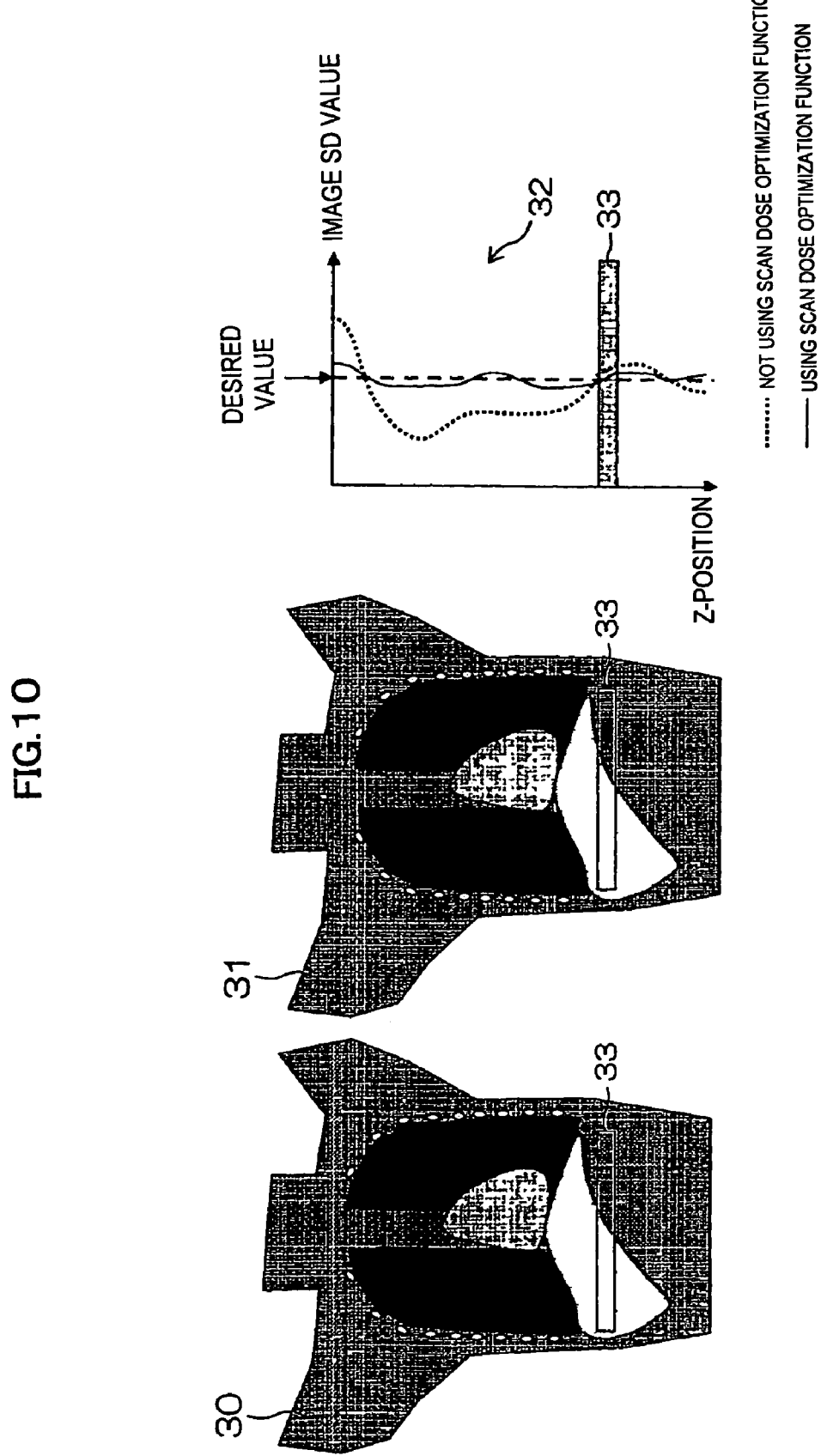
FIG. 10 is an example of displaying the target region along with the image comparative display.

1 . . . scanner, 2 . . . patient table, 3 . . . console, 4 . . . top panel, 5 . . . display device, 6 . . . operation device, 7 . . . X-ray tube control device, 8 . . . X-ray tube, 9 . . . collimator control device, 10 . . . collimator, 11 . . . detector, 12 . . . data collecting device, 13 . . . turntable, 14 . . . turntable control device, 15 . . . turntable driving device, 16 . . . driving force transmission system, 17 . . . object, 18 . . . X-ray detection element, 19 . . . system control device, 20 . . . patient table control device, 21 . . . patient table vertical motion device, 22 . . . top panel driving device, 23 . . . image reconstruction device, 24 . . . storage device, 25 . . . scan-planning device.

The invention claimed is:

1. An X-ray CT apparatus comprising:

an X-ray source provided with an X-ray tube for irradiating X-rays and an X-ray tube control device for controlling the X-ray tube;

an X-ray detector arranged facing the X-ray source having an object therebetween, for detecting the X-ray and outputting X-ray projection data;

rotation means to which the X-ray source and the X-ray detector are mounted and is capable of rotating them;

image processing means for reconstructing a tomographic image based on the X-ray projection data;

input means for inputting an image quality index value which indicates a desired index of image quality with respect to the tomographic image obtained by the image processing means;

model generation means for generating an object cross-sectional model in the body axis direction of the object from a scanogram data of the object;

optimization means for setting an irradiation modulation curve indicating a desired optimum X-ray irradiation dose based on the object cross-sectional model and the image quality index value, and modulating the X-ray irradiation dose based on the set irradiation modulation curve;

image quality estimation means for estimating the image quality of the supposed image using optimization by the optimization means when rotation scanning is performed by modulating the X-ray irradiation dose based on the irradiation modulation curve and the image quality of the supposed image without using optimization by the optimization means when the rotation imaging is performed without modulating the X-ray irradiation dose based on the irradiation dose modulation curve; and display means for displaying the image estimation result of the image estimation means.

2. The X-ray apparatus according to claim 1, wherein:

the image quality estimation means is image generation means for generating the supposed image using optimization by the optimization means and the supposed image without using optimization by the optimization means; and the image estimation result displayed by the display means is the supposed image using optimization by the optimization means and the supposed image without using optimization by the optimization means.

3. The X-ray CT apparatus according to claim 2, further comprising:

specification means for specifying a target region of the object from any one of a supposed image using optimization, a supposed image without using optimization or a scanogram image based on the scanogram data; and comparative information generation means for generating comparative information for comparing information of the target region in the supposed image using optimization and information of the target image in the supposed image without using optimization, wherein the display means further displays the comparative information.

4. The X-ray CT apparatus according to claim 3, wherein the comparative information generation means generates at least one information indicating position of the target region in the supposed image using optimization and the supposed image without using optimization, a graph showing image quality index value of the target region in the supposed image using optimization and the supposed image without using optimization, and numerical information indicating the image quality index value of the target region in the supposed image using optimization and the supposed image without using optimization.

5. The X-ray CT apparatus according to claim 1, wherein:
the image estimation means comprises image index value generating means for generating the image quality index value of the supposed image using optimization and the supposed image without using optimization, wherein the image quality estimation result displayed by the display means is the generated image quality index value.

6. The X-ray CT apparatus according to claim 5, wherein:
the image quality estimation means further comprises image index value comparison graph means for generating the image index value comparison graph based on the image quality index value generated by the image index value generation means, wherein the display means displays the image index value comparison graph.

7. The X-ray CT apparatus according to claim 6, wherein the display means displays a scanogram image based on the scanogram data along with the image index value comparison graph.

8. The X-ray CT apparatus according to claim 5, wherein the image quality index value calculated by the image index generation means is any one of an image SD value, contrast-noise ratio (SNR), and signal-noise ratio (SNR).

* * * * *